United States Patent [19]

Gunkel

[11] Patent Number: 4,981,615

[45] Date of Patent: Jan. 1, 1991

[54] PROCESS FOR FORMING A STABLE EMULSION FROM A TRIARYL PHOSPHATE REACTION MIXTURE RESIDUE

[75] Inventor: Louis T. Gunkel, Yardley, Pa.

[73] Assignee: FMC Corporation, Philadelphia, Pa.

[21] Appl. No.: 396,162

[22] Filed: Aug. 21, 1989

[51] Int. Cl.$^5$ .............................................. C09K 21/12
[52] U.S. Cl. ................................... 252/610; 252/608; 252/308
[58] Field of Search ............ 252/610, 608, 314, 400.23

[56] References Cited

U.S. PATENT DOCUMENTS

| | | | |
|---|---|---|---|
| 2,680,691 | 6/1954 | Olson et al. ............................ | 106/15 |
| 3,085,029 | 4/1963 | Miles et al. ............................ | 117/137 |
| 3,117,929 | 1/1964 | McCoy et al. ........................ | 252/314 |
| 3,247,015 | 4/1966 | Zimmerman et al. ............... | 252/608 |
| 3,553,128 | 1/1971 | Wilson ................................. | 252/610 |
| 3,576,923 | 4/1971 | Randell et al. ....................... | 260/966 |
| 3,856,535 | 12/1974 | Ferguson ........................ | 106/15 FP |
| 3,945,891 | 3/1976 | Aal et al. .............................. | 203/77 |
| 4,054,720 | 10/1977 | Tomita et al. ....................... | 428/480 |
| 4,097,641 | 6/1978 | Smith et al. ......................... | 252/610 |
| 4,196,005 | 4/1980 | Morgan et al. .................. | 106/18.16 |
| 4,360,452 | 11/1982 | Zabrocki et al. .................. | 252/314 |
| 4,556,684 | 12/1985 | Gunkel et al. ................. | 252/400.23 |

OTHER PUBLICATIONS

Kirk-Othmer, "*Encyclopedia of Chemical Technology*", 3rd Ed. vol. 8, Emulsions.

*Primary Examiner*—Robert L. Stoll
*Assistant Examiner*—Joseph D. Anthony
*Attorney, Agent, or Firm*—R. E. Elden; R. L. Andersen

[57] ABSTRACT

A novel process is provided for producing a pure triaryl phosphate ester free from phenolics without creating an undesirable waste product. After recovery of the triaryl phosphate ester the reactio mixture residue is converted into an emulsion suitable for use as a flame retardant useful for application to carpets.

18 Claims, No Drawings

PROCESS FOR FORMING A STABLE EMULSION FROM A TRIARYL PHOSPHATE REACTION MIXTURE RESIDUE

The invention is a process for purifying triaryl phosphate esters. More particularly, the invention is a novel, improved process for the conversion of impure triaryl phosphate esters into a pure triaryl phosphate product while concomitantly converting the residue into an emulsion suitable for use as a flame retardant.

Triaryl phosphate esters such as cresyl diphenyl phosphate, tricresyl phosphate, triphenyl phosphate, mixed xylyl cresyl phosphates, lower alkylphenyl/phenyl phosphates, such as mixed isopropylphenyl/phenyl phosphates, t-butylphenyl/phenyl phosphates, and the like are used extensively as plasticizers, functional fluids, gasoline additives, flame-retardant additives and the like. These products are conventionally prepared by the phosphorylation of a suitable phenolic feedstock, either the so-called natural cresols which are coal tar phenol fractions or synthetic feedstocks produced by alkylation of phenols as described, for example, in U.S. Pat. No. 3,576,923 issued Apr. 27, 1971 to Randell et al.

Increasingly more stringent limitations are being placed upon the allowable amount of unreacted and/or free phenols in chemical products. These requirements have created a demand for manufactured triaryl phosphate ester products which contain only trace quantities of unreacted phenols and alkyl phenols. At the same time, more and more stringent limitations are being placed on the disposal of chemical residues. U.S. Pat. No. 3,945,891 teaches a process to produce triaryl phosphates in which phenolics or alkylated phenolics are reacted with phosphorus oxychloride in the presence of aluminum chloride, the reaction product is flash distilled under vacuum to separate most of the triaryl phosphate product and phenolics or alkylated phenolics as overhead and leaving a triaryl phosphate reaction mixture residue typically containing aluminum alkoxides, aluminum chloroaryloxides, some triaryl phosphates and coproducts formed by the reaction. The phenolics and alkylated phenolics are subsequently fractionated in a distillation column, the phenolics as overheads to leave the underflow product a pure triaryl phosphate. This process does solve the problem of phenolics, but still leaves as a problem the disposal of the residue from the flash distillation.

The present invention overcomes the problems of the prior art by converting the triaryl phosphate reaction mixture residue into a stable water emulsion suitable for use as a flame retardant to be applied on carpet backing. The invention is a process for preparing a stable emulsion from a triaryl phosphate reaction mixture residue comprising aluminum aryloxides, aluminum chloroaryloxides, triaryl phosphate and coproducts formed by the catalyzed reaction of phenol or an alkylated phenol with phosphorus oxychloride, the process comprising forming an emulsion by incorporating into said reaction mixture residue;

a. sufficient aryl phosphate ester to adjust the viscosity of the reaction mixture residue to between $0.5 \times 10^{-4}$ and $10.0 \times 10^{-4}$ m$^2$/s, b. an effective amount of a chlorinated paraffin, c. an effective amount of an emulsifying agent, d. a neutralizing quantity of a neutralizing compound selected from the group selected from calcium hydroxide, alkali metal bicarbonate, alkali metal biphosphate, ammonium bicarbonate and ammonium biphosphate, and e. sufficient water to provide an emulsion containing from about 15% to about 30% by weight water; said water being incorporated therein by mixing with sufficient turbulence to form an emulsion.

The phosphate reaction mixture residue may be prepared by any batch or continuous process for reacting phenol or an alkylated phenol with phosphorus oxychloride in the presence of a catalyst such as aluminum chloride or magnesium chloride, any phenol or alkylated phenol being removed from the residue by distillation, extraction or the like. Preferably, the phosphate reaction mixture is distilled by the process of U.S. Pat. No. 3,945,891 or more preferably, the invention is incorporated as an improved process of subjecting the crude triaryl phosphate ester reaction mixture to flash distillation at a temperature of about 220° to 320° C. and a pressure of 2 to 10 mm Hg and removing catalyst residues and high boiling impurities as a reaction mixture residue in an underflow from the flash distillation and removing at least 90% of the feedstock as an overhead distillate comprising triaryl phosphate ester product and unreacted phenols, fractionally distilling the overhead from the flash distillation step in a fractional distillation column having a low pressure drop per theoretical stage maintained at a temperature of 4 to 10 mm Hg at the base of said fractional distillation column and a temperature of about 60° C. to 200° C. and a pressure of 2 to 4 mm Hg at the top of said column, and removing the purified triaryl phosphate ester product as a liquid underflow from the base of said column, the product being characterized as containing less than about 100 parts per million of unreacted phenols, free phenol, and alkyl phenols, the reaction mixture residue comprising catalyst residues and high boiling impurities in the flash distillation underflow being converted into a stable emulsion with water by incorporating therein an effective amount of a chlorinated paraffin, an effective amount of an emulsifying agent, sufficient aryl phosphate ester to adjust the viscosity of the reaction mixture residue to a viscosity of from about $0.5 \times 10^{-4}$ to $10 \times 10^{-4}$ m$^2$/s, a neutralizing quantity of a compound selected from the group consisting of calcium hydroxide, an alkali metal bicarbonate, an alkali metal biphosphate, ammonium bicarbonate and ammonium biphosphate, and water, said water being incorporated therein by mixing with sufficient turbulence to form a stable emulsion.

It was found that the residue has the same proportions of carbon, hydrogen, oxygen and phosphorus as the triaryl phosphate products, but appears to be a mixture of compounds rather than a single chemical. The residue may contain phenols and alkylated phenols which are a result of product breakdown or reaction in the hot still bottom, triaryl phosphate and a mixture of dimers and trimers and other higher molecular weight combinations. There are also minor amounts of aluminum and chlorine compounds present from the catalyst.

It was found that most of the residue samples failed to form emulsions. The reason is presumed to be because acid hydrolysis of the residue in the presence of the water forms phosphoric acids; phosphate esters are known to hydrolyze under acidic conditions.

Adjusting the pH with a strong base (sodium hydroxide) did not permit forming a stable emulsion. Effective compounds for neutralizing the residue were unexpectedly found to include a slightly soluble base, such as, calcium hydroxide or weak bases, such as sodium bicarbonate, mono and di sodium phosphate, and mono and di ammonium phosphate forming emulsions that remained creamy and uniform for weeks. Other possible weak bases such as amines did not work as well.

Generally about 0.2% to 3.0% by weight of the neutralizing compound is sufficient in the emulsion, preferably about 0.75% to about 1.5%.

The residue will vary in physical properties depending on the composition of the triaryl phosphate product and the amount of triaryl phosphate retained in the residue after recovering the product. For example, some of the residues are brickhard solids when cooled and must be heated quite hot to melt. Therefore it is necessary to adjust the viscosity of the residue in order to form an emulsion. This may be accomplished by incorporating a triaryl phosphate into the residue, either by blending product triaryl phosphate, or by retaining sufficient triaryl phosphate in the residue during the product stripping step. Generally a residue viscosity of $0.5 \times 10^{-4}$ to $10 \times 10^{-4}$ m$^2$/s (0.5 to 10 centistokes) is satisfactory. Sufficient triaryl phosphate may be incorporated into the residue in any convenient sequence, desirably prior to or simultaneously with the other ingredients.

It is well known that the combination of halogens with aryl phosphates improve the flame retardancy of the products. Suitable sources of chlorinated hydrocarbon include the commercially-available chlorinated paraffins. These compounds vary from about 20% to 70% chlorine by weight.

Chlorinated paraffins are miscible with many organic solvents; they are insoluble in water, glycerol and the glycols. Water emulsions can be made using the proper emulsifying agents. The amount of chlorinated paraffin employed to provide suitable flame retarding can be selected by one skilled in the art without undue experimentation. An effective quantity is generally an amount sufficient to provide from about 1% to 15% by weight chlorine to the nonaqueous portion of the emulsion, preferably about 5% to 10%.

Any suitable emulsifying agent can be employed. Generally one skilled in the art selects the emulsifying agent on a cost/performance basis. The emulsifying agent can be an anionic surfactant, a cationic surfactant or a nonionic surfactant such as an alkylphenol ethoxylate. An effective quantity of the emulsifying agent can be determined without undue experimentation by one skilled in the art. For example, it has been determined that 5 to 15 parts by weight of an emulsifying agent per hundred parts by weight water is effective when the emulsifying agent is $C_8H_{17}.C_6H_4(OC_2H_4)_5OH$.

The scope of this invention is intended to include the stable emulsion product made by the claimed process. The stable emulsion is produced by incorporating into a triaryl phosphate reaction mixture residue comprising aluminum aryloxides, aluminum chloroaryloxides, triaryl phosphate and coproducts formed by the catalyzed reaction of phenol or an alkylated phenol with phosphorus oxychloride;

a. sufficient aryl phosphate ester to adjust the viscosity of the reaction mixture residue to between $0.5 \times 10^{-4}$ and $10.0 \times 10^{-4}$ m$^2$/s, b. an effective amount of a chlorinated paraffin, c. an effective amount of an emulsifying agent, d. a neutralizing quantity of a neutralizing compound selected from the group selected from calcium hydroxide, alkali metal bicarbonate, alkali metal biphosphate, ammonium bicarbonate and ammonium biphosphate, and e. sufficient water to provide an emulsion containing from about 15% to about 30% by weight water; said water being incorporated therein by mixing with sufficient turbulence to form an emulsion.

For the purpose of this invention a stable emulsion is one which will not break into two phases for about 2 to 4 weeks. Generally, it is necessary to mix the components with turbulence to form an emulsion. Conventionally pumps, mixers and the like are selected according to the physical quantities and properties of the emulsion constituents. Other means such as ultrasonic mixing may also be employed.

The best mode of practicing the invention will be clear to one skilled in the art from the following examples.

CONTROL A

An emulsion was prepared by mixing a liquid triaryl phosphate ester, a chlorinated paraffin and an emulsifying agent to form a homogeneous solution. Water was then added to this mixture with high energy mixing such as obtained with a Cowles Dissolver stirring blade at such a rate as to form a water in oil emulsion that remained stable for several weeks. As the water was added the liquid changed from a thick mixture to a uniform, less viscous water in oil emulsion. The emulsion was white, creamy and uniform. The viscosity of the emulsion could be adjusted over a wide range by varying the proportions of the various components.

A typical formulation was:

250 grams of Kronitex* 100 brand triaryl phosphate 50 grams of Chlorowax* 50 brand chlorinated paraffin 10 grams of Triton* X100 brand emulsifying agent 100 grams of water.

*trademarks

Once the emulsion was formed it was placed in a glass bottle for observation. Failures usually separate into two layers upon standing overnight. A good emulsion will remain in suspension indefinitely. All of the good emulsions were stable for over eight weeks. Some borderline cases remained stable for a week or more and then slowly separated. These were considered as not passing the requirement.

CONTROL B

One hundred and thirty-six grams of a triaryl phosphate ester prepared from mixed isopropyl phenols and 114 grams of residue from the distillation step used to purify the phosphate ester were mixed together to form a viscous liquid. This blend was mixed with 50 grams of Chlorowax 50 chlorinated hydrocarbon and 5 grams of Triton X100 surfactant in a 1200 millimeter stainless steel beaker fitted with a Cowles serrated stirrer blade driven by a high speed air motor.

The components were mixed together at 25°-30° C. until a homogeneous blend was obtained The stirrer speed was then increased to its maximum capacity while 100 grams of water were added over a 30-40 minute time period. Following the addition of the water, the stirring was continued for an additional 30 minutes. During the stirring, a water in oil emulsion formed.

The emulsion was poured into a glass bottle and observed for stability.

The mixture separated after several days.

EXAMPLE 1

Example B was modified in that 3 grams of sodium bicarbonate were also charged to the blend prior to the addition of the water.

The mixture was emulsified in the same manner as Example B and placed in a clear glass bottle for observation.

Results of the observation: Emulsion stable for more than 4 weeks.

EXAMPLES 2 TO 28

Example 1 was repeated employing 250 g Kronitex 100 brand triaryl phosphate (TAP) plus residue, 50 g chlorinated paraffin, surfactant, 100 g water and neutralizing compound (additive). The proportions and results are presented as Table I. Examples 2 to 19 employed a mixture of residue plus Kronitex 50 brand triaryl phosphate prepared at a plant.

TABLE I

| Example | g TAP | Emulsifier | Residue | Additive g | Code | Result |
|---|---|---|---|---|---|---|
| 2 | 125 | 5 | 125 | 5 | TEA | NG |
| 3 | 125 | 5 | 125 | 3 | NaHCO3 | Good |
| 4 | 125 | 5 | 125 | 2 | NaHCO3 | NG |
| 5 | 60 | 5 | 190 | — | — | NG |
| 6 | 60 | 5 | 190 | 3 | NaHCO3 | Good |
| 7 | 60 | 5 | 190 | 3 | DSP | Good |
| 8 | 60 | 10 | 190 | 3 | DSP | Good |
| 9 | 60 | 15 | 190 | — | — | NG |
| 10 | 60 | 5 | 190 | 3 | DSP | Good |
| 11 | 60 | 5 | 190 | 3 | MSP | Good |
| 12 | 60 | 5 | 190 | 3 | ETNLAMNE | NG |
| 13 | 60 | 5 | 190 | 3 | (C2H2)3N | NG |
| 14 | 60 | 5 | 190 | 3 | Ca(OH)2 | Good |
| 15 | 60 | 5 | 190 | 3 | NH4HCO3 | Good |
| 16 | 60 | 5 | 190 | — | Na2B4O7 | NG |
| 17 | 60 | 5 | 190 | 3 | (C2H5)2NH | NG |
| 18 | 60 | 5 | 190 | 3 | DAP | Good |
| 19 | 60 | 5 | 190 | 3 | MAP | Good |
| 20 | 120 | 5 | 120 | 3 | MSP | Gel |
| 21 | 120 | 5 | 120 | 3 | DSP | Gel |
| 22 | 125 | 5 | 250 | 3 | NaHCO3 | Gel |
| 23 | — | 10 | 250 | 0 | — | NG |
| 24 | — | 10 | 250 | 3 | NaOH | NG |
| 25 | — | 10 | 250 | 3 | MAP | Good |
| 26 | — | 10 | 250 | 3 | MSP | Good |
| 27 | — | 10 | 250 | 3 | NaHCO3 | Good |
| 28 | — | 10 | 250 | 6 | NaOH | NG |

Additive
MSP = Mono Sodium Phosphate
DSP = Di Sodium Phosphate
3-ETNLAMNE = Triethanolamine
3-(C2H2)3N = Triethylamine
3-NH4HCO3 = Ammonium Bicarbonate
Na2B4O7 = Sodium Tetraborate
(C2H5)2NH = Diethylamine
MAP = Mono Ammonium Phosphate
DAP = Di Ammonium Phosphate

I claim:

1. A process for preparing a stable emulsion from a triaryl phosphate reaction mixture residue comprising aluminum aryloxides, aluminum, chloroaryloxides, triaryl phosphate and coproducts formed by the catalyzed reaction of phenol or an alkylated phenol with phosphorus oxychloride, the process comprising forming an emulsion by incorporating into said reaction mixture residue consisting essentially of aluminum aryloxides, aluminum chloroaryloxides, triaryl phosphate and coproducts formed by the catalyzed reaction of phenol or an alkylated phenol with phosphorus oxychloride;

a. sufficient aryl phosphate ester to adjust the viscosity of the reaction mixture residue to between $0.5 \times 10^{-4}$ and $10.0 \times 10^{-4}$ m$^2$/s,
b. a flame retarding amount of a chlorinated paraffin,
c. an emulsifying amount of an emulsifying agent,
d. a neutralizing quantity of a neutralizing compound selected from the group selected from calcium hydroxide, alkali metal bicarbonate, alkali metal biphosphate, ammonium bicarbonate and ammonium biphosphate, and
e. sufficient water to provide an emulsion containing from about 15% to about 30% by weight water; said water being incorporated therein by mixing with sufficient turbulence to form a stable, creamy emulsion.

2. The process of claim 1 wherein sufficient neutralizing compound is incorporated to provide 0.2% to 3.0% by weight in the emulsion.

3. The process of claim 1 wherein sufficient chlorinated paraffin is incorporated to provide 0.2% to 3.0% by weight in the emulsion.

4. The process of claim 2 wherein sufficient chlorinated paraffin is incorporated to provide 0.2% to 3.0% by weight in the emulsion.

5. The process of claim 1 wherein sufficient chlorinated paraffin is incorporated to provide from about 1% to 15% by weight chlorine to the nonaqueous portion of the emulsion.

6. The process of claim 2 wherein sufficient chlorinated paraffin is incorporated to provide from about 1% to 15% by weight chlorine to the nonaqueous portion of the emulsion.

7. The process of claim 3 wherein sufficient chlorinated paraffin is incorporated to provide from about 1% to 15% by weight chlorine to the nonaqueous portion of the emulsion.

8. The process of claim 4 wherein sufficient chlorinated paraffin is incorporated to provide from about 1% to 15% by weight chlorine to the nonaqueous portion of the emulsion.

9. The process of claim 1 wherein 5 to 15 parts by weight of an alkylphenylethoxylate is incorporated per hundred parts by weight water in the emulsion.

10. The process of claim 2 wherein 5 to 15 parts by weight of an alkylphenylethoxylate is incorporated per hundred parts by weight water in the emulsion.

11. The process of claim 3 wherein 5 to 15 parts by weight of an alkylphenylethoxylate is incorporated per hundred parts by weight water in the emulsion.

12. The process of claim 4 wherein 5 to 15 parts by weight of an alkylphenylethoxylate is incorporated per hundred parts by weight water in the emulsion.

13. The process of claim 5 wherein 5 to 15 parts by weight of an alkylphenylethoxylate is incorporated per hundred parts by weight water in the emulsion.

14. The process of claim 6 wherein 5 to 15 parts by weight of an alkylphenylethoxylate is incorporated per hundred parts by weight water in the emulsion.

15. The process of claim 7 wherein 5 to 15 parts by weight of an alkylphenylethoxylate is incorporated per hundred parts by weight water in the emulsion.

16. The process of claim 8 wherein 5 to 15 parts by weight of an alkylphenylethoxylate is incorporated per hundred parts by weight water in the emulsion.

17. In a process for purifying triaryl phosphate esters prepared by the phosphorylation of phenol, $C_1$-$C_4$ alkyl substituted phenols and mixtures of same by subjecting the crude triaryl phosphate ester reaction mixture to flash distillation at a temperature of about 220° to 320° C. and a pressure of 2 to 10 mm Hg and removing catalyst residues and high boiling impurities as a reaction mixture residue in an underflow and removing at least 90% of the feedstock as an overhead distillate comprising triaryl phosphate ester product and unreacted phenols, fractionally distilling the overhead from the flash distillation step in a fractional distillation column having a low pressure drop per theoretical stage maintained at a temperature of 250° to 300° C., a pressure of 4 to 10 mm Hg at the base of said column and a temperature of about 60° C. to 200° C. and a pressure of 2 to 4 mm Hg at the top of said column, and removing the purified triaryl phosphate ester product as a liquid underflow from the base of said column, the product being characterized as containing less than about 100 parts per million of unreacted phenols, free phenol, and alkyl phenols, the improvement comprising emulsifying said reaction mixture residue into a stable emulsion with water by incorporating therein a flame retarding amount of a chlorinated paraffin, an emulsifying amount of an emulsifying agent, sufficient arylphosphate ester to adjust the viscosity thereof to a viscosity of from about $0.5 \times 10^{-4}$ to $10 \times 10^{-4}$ m$^2$/s, a neutralizing quantity of a compound selected from the group consisting of calcium hydroxide, an alkali metal bicarbonate, an alkali metal biphosphate, ammonium bicarbonate and ammonium biphosphate, and water, said water being incorporated therein by mixing with sufficient turbulence to form a stable, creamy emulsion.

18. A stable emulsion produced by the process comprising incorporating into a triaryl phosphate reaction mixture residue, said residue comprising aluminum aryloxides, aluminum chloroaryloxides, triaryl phosphate and coproducts formed by the catalyzed reaction of phenol or an alkylated phenol with phosphorus oxychloride,
 a. sufficient aryl phosphate ester to adjust the viscosity of the reaction mixture residue to between $0.5 \times 10^{-4}$ and $10.0 \times 10^{-4}$ m$^2$/s,
 b. an effective amount of a chlorinated paraffin to provide 1% to 15% by weight chlorine,
 c. 5 to 15 parts by weight of an emulsifying agent per hundred parts by weight water wadded in part (e),
 d. a neutralizing quantity of a neutralizing compound selected from the group selected from calcium hydroxide, alkali metal bicarbonate, alkali metal biphosphate, ammonium bicarbonate and ammonium biphosphate, and
 e. sufficient water to provide an emulsion containing from about 15% to about 30% by weight water; said water being incorporated therein by mixing with sufficient turbulence to form a stable, creamy emulsion.

* * * * *